(12) United States Patent
Iwata et al.

(10) Patent No.: US 9,204,641 B2
(45) Date of Patent: Dec. 8, 2015

(54) COMPOSITION AND METHOD FOR CONTROLLING PLANT DISEASES

(75) Inventors: Atsushi Iwata, Tokyo (JP); Makoto Kurahashi, Hyogo (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/239,811

(22) PCT Filed: Aug. 23, 2012

(86) PCT No.: PCT/JP2012/071926
§ 371 (c)(1),
(2), (4) Date: Feb. 20, 2014

(87) PCT Pub. No.: WO2013/027858
PCT Pub. Date: Feb. 28, 2013

(65) Prior Publication Data
US 2014/0221441 A1 Aug. 7, 2014

(30) Foreign Application Priority Data
Aug. 24, 2011 (JP) ................................. 2011-182312

(51) Int. Cl.
*A01N 37/30* (2006.01)
*A01N 43/38* (2006.01)
*A01N 43/653* (2006.01)

(52) U.S. Cl.
CPC ................ *A01N 43/38* (2013.01); *A01N 37/30* (2013.01); *A01N 43/653* (2013.01)

(58) Field of Classification Search
CPC ....... A01N 37/30; A01N 43/38; A01N 43/50; A01N 43/653
USPC .......... 504/100, 284, 315, 319; 514/383, 406, 514/407
See application file for complete search history.

(56) References Cited

U.S. PATENT DOCUMENTS

2010/0267565 A1* 10/2010 Kurahashi et al. ............ 504/322

FOREIGN PATENT DOCUMENTS

| JP | 11-255607 | 9/1999 |
| JP | 2001-139405 | 5/2001 |
| WO | 99/45774 | 9/1999 |
| WO | 2010/049414 | 5/2010 |
| WO | 2010/123849 | 10/2010 |
| WO | 2011/071187 | 6/2011 |
| WO | 2012/046821 | 4/2012 |
| WO | 2013/027859 | 2/2013 |
| WO | 2013/027860 | 2/2013 |
| WO | 2013/027862 | 2/2013 |
| WO | 2013/027863 | 2/2013 |
| WO | 2013/062136 | 5/2013 |
| WO | 2013/062137 | 5/2013 |
| WO | 2013/062138 | 5/2013 |
| WO | 2013/062139 | 5/2013 |
| WO | 2013/062141 | 5/2013 |

OTHER PUBLICATIONS

International Preliminary Report on Patentability and Written Opinion dated Feb. 25, 2014 in International Application No. PCT/JP2012/071926.
The Pesticide Manual—15th Edition, Published by British Crop Protection Council (BCPC), ISBN978-1-901396-18-8, pp. 1071-1146, 2011.

* cited by examiner

*Primary Examiner* — John Pak
(74) *Attorney, Agent, or Firm* — Wenderoth, Lind & Ponack, L.L.P.

(57) ABSTRACT

The present invention provides a composition for controlling plant diseases having an excellent control efficacy on plant diseases. A composition for controlling plant diseases comprising an amide compound represented by a formula (I): wherein each of symbols are the same as defined in the Description; or salts thereof and one or more kinds of azole compounds selected from the group (A) consisting of tebuconazole, difenoconazole, triticonazole, imazalil, triadimenol, fluquinconazole, prochloraz, prothioconazole, diniconazole, diniconazole M, cyproconazole, tetraconazole, ipconazole, triforine, pyrifenox, fenarimol, nuarimol, oxpoconazole fumarate, pefurazoate, triflumizole, azaconazole, bitertanol, bromuconazole, epoxiconazole, fenbuconazole, flusilazole, flutriafol, hexaconazole, imibenconazole, myclobutanil, penconazole, propiconazole, simeconazole, triadimefon and metconazole, shows an excellent controlling efficacy on plant diseases.

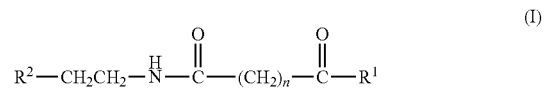

(I)

8 Claims, No Drawings

COMPOSITION AND METHOD FOR CONTROLLING PLANT DISEASES

TECHNICAL FIELD

The present invention relates to a composition for controlling plant diseases and a method for controlling plant diseases.

BACKGROUND ART

Hitherto, many compounds have been known as active ingredients in a composition for controlling plant diseases (The Pesticide Manual-15th edition, published by British Crop Protection Council (BCPC), ISBN978-1-901396-18-8).

DISCLOSURE of INVENTION

Problems to be Solved by Invention

An object of the present invention is to provide a composition for controlling plant diseases having an excellent control efficacy on plant diseases.

Means to Solve Problems

The present inventors have intensively studied to find out a composition for controlling plant diseases having an excellent control efficacy on plant diseases. As a result, they have found that a composition comprising an amide compound represented by the following formula (I) or salts thereof and one or more kinds of azole compounds selected from the group consisting of the following group (A) has an excellent controlling effect on plant diseases. Thus, the present invention has been completed.

Specifically, the present invention includes:

[1] A composition for controlling plant diseases comprising an amide compound represented by a formula (I):

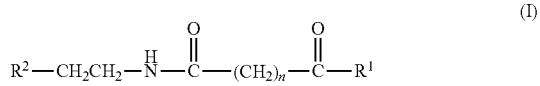

wherein
n is 3 or 4;
$R^1$ represents a hydroxy group, an amino group or a C1-C6 alkoxy group;
$R^2$ represents an optionally substituted phenyl group, an optionally substituted 1-naphthyl group or an optionally substituted 3-indolyl group, and the phenyl group, the 1-naphthyl group or the 3-indolyl group being represented by the $R^2$ may be substituted on the carbon atoms independently of each other with one or more substituents selected from a halogen atom, a hydroxy group, a nitro group, a C1-C6 alkyl group or a C1-C6 alkoxy group;
or salts thereof and
at least one kind of azole compounds selected from the group (A) consisting of tebuconazole, difenoconazole, triticonazole, imazalil, triadimenol, fluquinconazole, prochloraz, prothioconazole, diniconazole, diniconazole M, cyproconazole, tetraconazole, ipconazole, triforine, pyrifenox, fenarimol, nuarimol, oxpoconazole fumarate, pefurazoate, triflumizole, azaconazole, bitertanol, bromuconazole, epoxiconazole, fenbuconazole, flusilazole, flutriafol, hexaconazole, imibenconazole, myclobutanil, penconazole, propiconazole, simeconazole, triadimefon and metconazole.

[2] The composition for controlling plant diseases according to [1] wherein a weight ratio of the amide compound or salts thereof to the azole compounds is in the range of 100:1 to 1:100.

[3] The composition for controlling plant diseases according to [1] wherein at least one kind of azole compounds is selected from the group (A) consisting of tebuconazole, difenoconazole, triticonazole, imazalil, triadimenol, fluquinconazole, prochloraz, prothioconazole, diniconazole, diniconazole M, cyproconazole, tetraconazole, ipconazole, triforine, pyrifenox, fenarimol, nuarimol, fenbuconazole, flusilazole, flutriafol, hexaconazole, imibenconazole; myclobutanil, penconazole, propiconazole, simeconazole and triadimefon.

[4] The composition for controlling plant diseases according to [3] wherein a weight ratio of the amide compound or salts thereof to the azole compounds is in the range of 100:1 to 1:100.

[5] A method for controlling plant diseases which comprises applying an effective amount of the composition for controlling plant diseases according to [1] or [2] to a plant or a soil for cultivating the plant.

[6] A method for controlling plant diseases which comprises applying an effective amount of the composition for controlling plant diseases according to [1] or [2] to plant seeds.

[7] The method for controlling plant diseases according to [6] wherein the plant seeds are seeds of corn, cotton, soybean, beet, rapeseed, wheat or rice.

[8] A method for controlling plant diseases which comprises applying an effective amount of the composition for controlling plant diseases according to [3] or [4] to a plant or a soil for cultivating the plant.

[9] A method for controlling plant diseases which comprises applying an effective amount of the composition for controlling plant diseases according to [3] or [4] to plant seeds.

[10] The method for controlling plant diseases according to [9] wherein the plant seeds are seeds of corn, cotton, soybean, beet, rapeseed, wheat or rice.

Effect of Invention

The present invention can control plant diseases.

MODE FOR CARRYING OUT THE INVENTION

Hereinafter, the present invention is explained in detail.
The term "composition for controlling plant diseases of the present invention" refers to a composition comprising an amide compound represented by a formula (I):

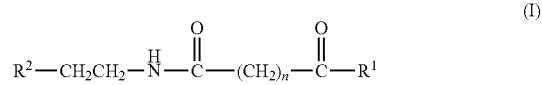

wherein
n is 3 or 4;
$R^1$ represents a hydroxy group, an amino group or a C1-C6 alkoxy group;
$R^2$ represents an optionally substituted phenyl group, an optionally substituted 1-naphthyl group or an optionally substituted 3-indolyl group, and the phenyl group, the 1-naphthyl group or the 3-indolyl group being represented by the R² may be substituted on the carbon atoms independently of each other with one or more substituents selected from a halogen atom, a hydroxy group, a nitro group, a C1-C6 alkyl group or a C1-C6 alkoxy group (hereinafter referred as to "the present amide compound");
or salts thereof and
at least one kind, of azole compounds selected from the group (A) consisting of tebuconazole, difenoconazole, triticonazole, imazalil, triadimenol, fluquinconazole, prochloraz, prothioconazole, diniconazole, diniconazole M, cyproconazole, tetraconazole, ipconazole, triforine, pyrifenox, fenarimol, nuarimol, oxpoconazole fumarate, pefurazoate, triflumizole, azaconazole, bitertanol, bromuconazole, epoxiconazole, fenbuconazole, flusilazole, flutriafol, hexaconazole, imibenconazole, myclobutanil, penconazole, propiconazole, simeconazole, triadimefon and metconazole (hereinafter referred as to "the present azole compounds").

In the formula (I), as the group represented by the R¹,
the term "C1-C6 alkoxy group" includes, for example, a methoxy group, an ethoxy group, a propoxy group, a butoxy group, a pentyloxy group, a hexyloxy group, a 1-methylethoxy group, a 2-methylpropoxy group, 3-methylbutoxy group and 4-methylpentyloxy group.

In the formula (I), when the phenyl group, the 1-naphthyl group or the 3-indolyl group being represented by the R² may be substituted on the carbon atoms independently of each other with one or more substituents (preferably one or two substituents and more preferably one substituent), as the substituent,
the term "halogen atom" includes, for example, fluorine atom, a chlorine atom, a bromine atom and an iodine atom;
the term "C1-C6 alkyl group" includes, for example, a methyl group, an ethyl group, a propyl group, a butyl group, a pentyl group, a hexyl group, a 1-methylethyl group, a 2-methylpropyl group, a 3-methylbutyl group and a 4-methylpentyl group; and
the term "C1-C6 alkoxy group" includes, for example, a methoxy group, an ethoxy group, a propoxy group, a butoxy group, a pentyloxy group, a hexyloxy group, a 1-methylethoxy group, a 2-methylpropoxy group, a 3-methylbutoxy group and a 4-methylpentyloxy group.

When in the formula (I), the phenyl group, the 1 naphthyl group or the 3-indolyl group being represented by the R² may be substituted on the carbon atoms simultaneously with each other with two or more substituents selected from the halogen atom, the hydroxy group, the nitro group, the C1-C6 alkyl group or the C1-C6 alkoxy group, the substituent on each of the carbon atoms may be the same or different to each other.

The salts of the present amide compound include, for example, inorganic base salts and organic base salts.

The inorganic base salts include, for example, alkali metal salts such as sodium salts and potassium salts, alkaline-earth metal salts such as calcium salts and magnesium salts, and ammonium salts.

The organic base salts include, for example, amine salts such as triethylamine salts, pyridine salts, picoline salts, ethanolamine salts, triethanolamine salts, dicyclohexylamine salts, and N,N'-dibenzylethylenediamine salts.

Examples of the present amide compound includes
the amide compound represented by the formula (I) wherein n is 3, R¹ represents a hydroxy group, an amino group or a C1-C6 alkoxy group, and R² is an 3-indolyl group;
the amide, compound represented by the formula (I) wherein n is 3 or 4, and R¹ represents a hydroxy group and R² is an 3-indolyl group;

the amide compound represented by the formula (I) wherein n is 3, R¹ represents a hydroxy group or a C1-C2 alkoxy group and R² is a phenyl group, a 1-naphthyl group, an 3-indolyl group or a 5-methyl-3-indolyl group; and
the amide compound represented by the formula (I) wherein n is 4, R¹ represents a hydroxy group or a C1-C2 alkoxy group and R² is a phenyl group.

Next, specific examples of the present amide compound are shown below.

The amide compound represented by the formula (I-a):

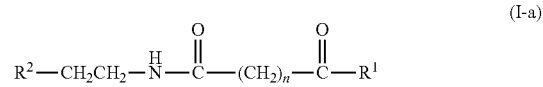

wherein a combination of n, R¹ and R² represents any combination as shown in Table 1.

TABLE 1

| Compound No. | n | R¹ | R² |
|---|---|---|---|
| 1 | 3 | OH | phenyl |
| 2 | 3 | OCH₃ | phenyl |
| 3 | 3 | OH | 3-indolyl |
| 4 | 3 | OCH₃ | 3-indolyl |
| 5 | 3 | OCH₂CH₃ | 3-indolyl |
| 6 | 3 | OCH₂CH₂CH₃ | 3-indolyl |
| 7 | 3 | OH | 5-methyl-3-indolyl |
| 8 | 3 | OH | 1-naphthyl |
| 9 | 3 | OCH₃ | 1-naphthyl |
| 10 | 3 | OCH₂CH₃ | 1-naphthyl |
| 11 | 4 | OH | phenyl |
| 12 | 4 | OCH₃ | phenyl |

The present amide compounds are those described in, for example, JP-11-255607 A and JP-2001-139405 A, and can be prepared, for example, according to the methods described therein.

Also, tebuconazole, difenoconazole, triticonazole, imazalil, triadimenol, fluquinconazole, prochloraz, prothioconazole, diniconazole, diniconazole M, cyproconazole, tetraconazole, ipconazole, triforine, pyrifenox, fenarimol, nuarimol, oxpoconazole fumarate, pefurazoate, triflumizole, azaconazole, bitertanol, bromuconazole, epoxiconazole, fenbuconazole, flusilazole, flutriafol, hexaconazole, imibenconazole, myclobutanil, penconazole, propiconazole, simeconazole, triadimefon and metconazole that are used in the present invention are all known compounds, and are described in, for'example, "The PESTICIDE MANUAL— 15th EDITION (BCPC published) ISBN 978-1-901396-18-8", pages 1072, 354, 1182, 629, 1147, 543, 928, 965, 384, 384, 287, 1096, 663, 1177, 1255, 465, 1250, 854, 868, 1171, 52, 116, 134, 429, 468, 554, 560, 611, 643, 801, 869, 952, 1033, 1145 and 749 respectively.
These compounds are either commercially available, or can be prepared by known methods.

Tebuconazole, difenoconazole, triticonazole, imazalil, triadimenol, fluquinconazole, prochloraz, prothioconazole, diniconazole, diniconazole M, cyproconazole, tetraconazole, ipconazole, triforine, pyrifenox, fenarimol, nuarimol, oxpoconazole fumarate, pefurazoate, triflumizole, azaconazole, bitertanol, bromuconazole, epoxiconazole, fenbuconazole, flusilazole, flutriafol, hexaconazole, imibenconazole, myclobutanil, penconazole, propiconazole, simeconazole, triadimefon and metconazole that are used in the present invention are fungicidal compounds that known as demethylation inhibitor (abbreviation: DMI agent).

The weight ratio of the present amide compound or salts thereof to the present azole compounds in the composition for controlling plant diseases of the present invention includes, but is not limited to, in the range of usually 2 to 10,000,000 parts by weight and preferably 10 to 100,000 parts by weight of the present azole compounds opposed to 1,000 parts by weight of the present amide compound or salts thereof.

Although the composition for controlling plant diseases of the present invention may be a mixture as itself of the present amide compound or salts thereof and the present azole compounds, the composition of the present invention is usually prepared by mixing the present amide compound or salts thereof, the present azole compounds and an inert carrier, and if necessary, adding a surfactant or other pharmaceutical additives, and then formulating into the form of oil solution, emulsifiable concentrate, flowable formulation, wettable powder, granulated wettable powder, dust formulation, granules and so on.

Also the composition for controlling plant diseases formulated as aforementioned can be used by itself or with an addition of an inert carrier as an agent for controlling plant diseases.

In the composition for controlling plant diseases of the present invention, a total amount of the present amide compound or salts thereof and the present azole compounds is in the range of usually 0.1% to 99% by weight, preferably 0.2% to 90% by weight, and more preferably 1% to 80% by weight.

Also the composition for controlling plant diseases of the present invention may further optionally contain one or more pesticides and/or fungicides other than those mentioned above.

Examples of the inert carrier used in the formulation include an inert solid carrier and an inert liquid carrier.

Examples of the solid carrier used in the formulation include finely-divided powder or particles consisting of minerals (for example, kaolin clay, attapulgite clay, bentonite, montmorillonite, acid clay, pyrophyllite, talc, diatomaceous earth, or calcite), natural organic substances (for example, corncob powder, or walnut shell powder), synthetic organic substances (for example, urea), salts (for example, calcium, carbonate, or ammonium sulfate), synthetic inorganic substances (for example, synthetic hydrous silicon oxide) and the others. Examples of the liquid carrier include aromatic hydrocarbons (for example, xylene, alkyl benzene, or methylnaphtalene), alcohols (for example, 2-propanol, ethylene glycol, propylene glycol, or ethylene glycol monoethyl ether), ketones (for example, acetone, cyclohexanone, or isophorone), vegetable oils (for example, soybean oil, or cotton oils), petroleum-derived aliphatic hydrocarbons, esters, dimethylsulfoxide, acetonitrile and water.

Examples of the surfactant include anionic surfactant (for example, alkyl sulfate salts, alkylaryl sulfate salts, dialkyl sulfosuccinate salts, polyoxyethylene alkylaryl ether phosphates, lignin sulfonate, or naphthalenesulfonate formaldehyde polycondensation), nonionic surfactant (for example, polyoxyethylene alkylaryl ether, polyoxyethylene alkyl polyoxypropylene block copolymer, or sorbitan fatty acid ester) and cationic surfactant (for example, alkyltrimethyl ammonium salts).

Examples of the other pharmaceutical additives include water-soluble polymer (for example, polyvinyl alcohol, or polyvinyl pyrrolidone), polysaccharides (for example, arabic gum, alginic acid and salts thereof, CMC (carboxymethylcellulose), or xanthan gum), inorganic substances (for example, aluminum magnesium silicate, or alumina-sol), antiseptic agent, coloring agent, and stabilizing agent (for example, BHT, or PAP (isopropyl acid phosphate)).

The composition for controlling plant diseases of the present invention is used to control a plant disease by applying it to a plant or a soil for cultivating the plant.

The plant diseases which can be controlled by the present invention are exemplified below:

Rice diseases: blast (*Magnaporthe oryzae*) helminthosporium leaf spot (*Cochliobolus miyabeanus*) and bakanae disease (*Gibberella fujikuroi*)

Diseases of barley, wheat, oats and rye: powdery mildew (*Erysiphe graminis*), Fusarium head blight (*Fusarium graminearum, F. avenaceum, F. culmorum, F. asiaticum, Microdochium nivale*), rust (*Puccinia striiformis, P. graminis, P. recondita, P. hordei*), snow blight (*Typhula* sp., *Micronectriella nivalis*), loose smut (*Ustilago tritici, U. nuda*), bunt (*Tilletia caries*) eyespot (*Pseudocercosporella herpotrichoides*) scald (*Rhynchosporium secalis*), leaf blotch (*Septoria tritici*), glume blotch (*Leptosphaeria nodorum*) and net blotch (*Pyrenophora teres Drechsler*);

Citrus diseases: melanose (*Diaporthe citri*) and scab (*Elsinoe fawcetti*);

Apple diseases: blossom blight (*Monilinia mali*), canker (*Valsa ceratosperma*), powdery mildew (*Podosphaera leucotricha*), *Alternaria* leaf spot (*Alternaria alternata* apple pathotype) scab (*Venturia inaequalis*) and bitter rot (*Colletotrichum acutatum*);

Pear diseases: scab (*Venturia nashicola, V. pirina*), black spot (*Alternaria alternata* Japanese pear pathotype) and rust (*Gymnosporangium haraeanum*);

Peach diseases: brown rot (*Monilinia fructicola*), scab (*Cladosporium carpophilum*) and *Phomopsis* rot (*Phomopsis* sp.);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*) and gray mold (*Botrytis cinerea*);

Diseases of Japanese persimmon: anthracnose (*Gloeosporium kaki*) and leaf spot (*Cercospora kaki, Mycosphaerella nawae*);

Diseases of gourd family: anthracnose (*Colletotrichum lagenarium*) powdery mildew (*Sphaerotheca fuliginea*), gummy stem blight (*Mycosphaerella melonis*) and *Fusarium* wilt (*Fusarium oxysporum*);

Tomato diseases: early blight (*Alternaria solani*) and leaf mold (*Cladosporium fulvum*);

Egg plant disease: brown spot (*Phomopsis vexans*) and powdery mildew (*Erysiphe cichoracearum*);

Diseases of Cruciferous Vegetables: *Alternaria* leaf spot (*Alternaria japonica*) and white spot (*Cercosporella brassicae*);

Rapeseed diseases: *Sclerotinia* rot (*Sclerotinia sclerotiorum*), black spot (*Alternaria brassicae*), powdery mildew (*Erysiphe cichoracearum*), blackleg (*Leptosphaeria maculans*);

Welsh onion diseases: rust (*Puccinia allii*);

Soybean diseases: purple seed stain (*Cercospora kikuchii*), sphaceloma scad (*Elsinoe glycines*), pod and stem blight (*Diaporthe phaseolorum* var. *sojae*) and rust (*Phakopsora pachyrhizi*);

Adzuki-bean diseases: gray mold (*Botrytis cinerea*), sclerotinia rot (*Sclerotinia sclerotiorum*);

Kindney bean diseases: gray mold (*Botrytis cinerea*), *Sclerotinia* rot (*Sclerotinia sclerotiorum*), anthracnose (*Colletotrichum lindemthianum*);

Peanut diseases: leaf spot (*Cercospora personata*), brown leaf spot (*Cercospora arachidicola*) and southern blight (*Sclerotium rolfsii*);

Garden pea diseases: powdery mildew (*Erysiphe pisi*);

Strawberry diseases: powdery mildew (*Sphaerotheca humuli*);

Tea diseases: net blister blight (*Exobasidium reticulatum*), white scab (*Elsinoe leucospila*), gray blight (*Pestalotiopsis* sp.) and anthracnose (*Colletotrichum theae-sinensis*);

Cotton diseases: Fusarium wilt (*Fusarium oxysporum*), damping-off (*Rhizoctonia solani*);

Tabacco diseases: brown spot (*Alternaria longipes*), powdery mildew (*Erysiphe cichoracearum*) and anthracnose (*Colletotrichum tabacum*);

Sugar beet diseases: cercospora leaf spot (*Cercospora beticola*), leaf blight (*Thanatephorus cucumeris*) and root rot (*Thanatephorus cucumeris*);

Rose diseases: black spot (*Diplocarpon rosae*) and powdery mildew (*Sphaerotheca pannosa*);

Chrysanthemum diseases: leaf blight (*Septoria chrysanthemi-indici*) and white rust (*Puccinia horiana*);

Various plants diseases: gray mold (*Botrytis cinerea*), Sclerotinia rot (*Sclerotinia sclerotiorum*), Japanese radish Disease: Alternaria leaf spot (*Alternaria brassicicola*);

Turfgrass diseases: dollar spot (*Sclerotinia homeocarpa*) brown patch and large patch (*Rhizoctonia solani*); and Banana diseases: Sigatoka disease (*Micosphaerella fijiensis, Mycosphaerella musicola, Pseudocercospora musae*).

The composition for controlling plant diseases of the present invention can be used in agricultural lands such as fields, paddy fields, dry paddy fields, lawns and orchards or in non-agricultural lands. Also the composition for controlling plant diseases of the present invention can control plant diseases in agricultural lands and the others for cultivating the following "plant" and the others.

The plant which can be applied by the composition for controlling plant diseases of the present invention is exemplified below:

Crops:
corn, rice, wheat, barley, rye, oat, sorghum, cotton, soybean, peanut, buckwheat, beet, rapeseed, sunflower, sugar cane, tobacco, and the others;

Vegetables:
solanaceous vegetables (for example, eggplant, tomato, pimento, pepper and potato),
cucurbitaceous vegetables (for example, cucumber, pumpkin, zucchini, water melon and melon),
cruciferous vegetables (for example, Japanese radish, white turnip, horseradish, kohlrabi, Chinese cabbage, cabbage, leaf mustard, broccoli, cauliflower, colza),
asteraceous vegetables (for example, burdock, crown daisy, artichoke and lettuce),
liliaceous vegetables (for example, green onion, onion, garlic and asparagus),
ammiaceous vegetables (for example, carrot, parsley, celery and parsnip),
chenopodiaceous vegetables (for example, spinach and *Swiss chard*),
lamiaceous vegetables (for example, *Perilla frutescens*, mint and basil),
strawberry, sweet potato, Dioscorea japonica, colocasia and the others;

Fruits:
pomaceous fruits (for example, apple, pear, Japanese pear, Chinese quince and quince),
stone fleshy fruits (for example, peach, plum, nectarine, *Prunus mume*, cherry fruit, apricot and prune),
citrus fruits (for example, *Citrus unshiu*, orange, lemon, lime and grapefruit),
nuts (for example, chestnut, walnuts, hazelnuts, almond, pistachio, cashew nuts and *macadamia* nuts),
berry fruits (for example, blueberry, cranberry, blackberry and raspberry),
grape, kaki persimmon, olive, Japanese plum, banana, coffee, date palm, coconuts, oil palm and the others;

Trees other than fruit trees:
tea, mulberry,
flowering plant (for example, dwarf azalea, camellia, hydrangea, sasanqua, *Illicium anisatum*, cherry trees, tulip tree, crape myrtle and fragrant olive),
roadside trees (for example, ash, birch, dogwood, *Eucalyptus, Ginkgo biloba*, lilac, maple, *Quercus*, poplar, Judas tree, *Liquidambar formosana*, plane tree, zelkova, Japanese arborvitae, fir wood, hemlock, juniper, *Pinus, Picea, Taxus cuspidate*, elm and Japanese horse chestnut),
Sweet viburnum, *Podocarpus macrophyllus*, Japanese cedar, Japanese cypress, croton, Japanese spindletree and *Photinia glabra*;

Lawn:
sods (for example, *Zoysia japonica, Zoysia matrella*),
bermudagrasses (for example, *Cynodon dactylon*),
bent glasses (for example, *Agrostis gigantea, Agrostis stolonifera, Agrostis capillaris*), blueglasses (for example, *Poa pratensis, Poa trivialis*),
festucae (for example, *Festuca arundinacea Schreb., Festuca rubra* L. var. *commutate Gaud., Festuca rubra* L. var. *genuina* Hack),
ryegrassses (for example, *Lolium multiflorum Lam, Lolium perenne* L), *Dactylis glomerata, Phleum pratense*;

Others:
flowers (for example, rose, carnation, chrysanthemum, Eustoma, gypsophila, gerbera, marigold, salvia, petunia, verbena, tulip, aster, gentian, lily, pansy, cyclamen, orchid, lily of the valley, lavender, stock, ornamental cabbage, primula, poinsettia, gladiolus, cattleya, daisy, cymbidium and begonia),
bio-fuel plants (for example, Jatropha, safflower, *Camelina*, switch grass, *Miscanthus giganteus, Phalaris arundinacea, Arundo donax*, kenaf, cassava, willow), and
ornamental foliage plants, and the others.

Among the above-mentioned plants, preferred examples include corn, beet, rice, sorghum, soybean, cotton, rapeseed and wheat.

The above-mentioned "plant" includes plants, to which a resistance has been conferred by a classical breeding method or genetic engineering technique.

The composition for controlling plant diseases of the present invention is used to control plant diseases by applying it to the plant or an area for cultivating the plant. Such plants to be used herein include foliages of plant, flowers of plant, fruits of plant, seeds of plant, or bulbs of plant. The bulbs to be used herein are intended to mean bulb, corm, rootstock, tubera, tuberous root and rhizophore.

The method for controlling plant diseases of the present invention comprises applying the composition for controlling plant diseases of the present invention.

Specific examples of the method of applying the composition for controlling plant diseases of the present invention include an application to stems and leaves of plants such as a foliage application; an application to seeds of plants; and an application to area for cultivating plants such as a soil treatment and a submerged application.

Specific examples of the application to stems and leaves of plants such as a foliage application in the present invention include an application to surfaces of plants to be cultivated, for example, by a ground application with a manual sprayer, a power sprayer, a boom sprayer or Pancle sprayer or by an aerial application by using manned or unmanned airplane or helicopter.

Specific examples of the application to seeds of plants in the present invention include an application of the composition for controlling plant diseases of the present invention to seeds or bulbs of plants, more specifically, a spray coating treatment on the surface of seeds or bulbs, a smear treatment on the seeds or bulbs of plants, an immersion treatment, a film coating treatment and a pellet coating treatment.

Specific examples of the application to area for cultivating plants such as a soil application and submerged application in the present invention include:
a planting hole application, a plant foot application, a row application, an in-furrow application, an overall application, a side ditch application, a nursery box application, a nursery bed application, a nursery soil incorporation, a bed soil incorporation, a paste fertilizer incorporation, a paddy water application, and a submerged application under flooding condition.

When the composition for controlling plant diseases of the present invention is applied to plants or area for cultivating plants, the application dose varies depending on the kinds of plants to be protected, the species or the degree of emergence of plant diseases to be controlled, the dosage form, the timing of application, weather conditions, etc., but the total amount of the present amide compound or salt thereof and the azole compounds is in the range of usually from 0.05 to 10,000 g, preferably from 0.5 to 1,000 g per 1,000 $m^2$ of the area for cultivating plants.

When the composition for controlling plant diseases of the present invention is applied to seeds of plants, the application dose varies depending on the kinds of plants to be protected, the species or the degree of emergence of plant diseases to be controlled, the dosage form, the timing of application, weather conditions, etc., but the total amount of the present amide compound or salts thereof and the azole compounds is in the range of usually from 0.001 to 100 g, preferably from 0.05 to 50 g per 1 kg of the seeds.

The emulsifiable concentrate, the wettable powder or the flowable formulation, etc. of the composition for controlling plant diseases of the present invention is usually applied by diluting it with water, and then spreading it. In this case, the total concentration of the present amide compound or salts thereof and the azole compounds is in the range of usually 0.00001 to 10% by weight, and preferably 0.0001 to 5% by weight. The dust formulation or the granular formulation, etc, is usually applied as itself without diluting it.

EXAMPLES

The following Examples including Formulation examples and Test examples serve to illustrate the present invention in more detail, which should not intend to limit the present invention. In the Examples, the term "part(s)" means part(s) by weight unless otherwise specified, and "the present amide compound (Compound No. X)" corresponds to "Compound No. X" listed in Table 1, that is, for example, "the present amide compound (Compound No. 1)" refers to Compound No. 1 listed in Table 1.

Formulation examples are shown below.

Formulation Example 1

Ten (10) parts of the present amide compound selected from Compound No. 1 to Compound No. 12, 1 part of tebuconazole, 35 parts of a mixture (weight ratio 1:1) of white carbon and ammonium polyoxyethylene alkyl ether sulfate are mixed with an appropriate amount of water so as to give a total amount of 100 parts, and then the mixture is finely-ground by a wet grinding method to obtain a flowable formulation.

Formulation Example 2

Ten (10) parts of the present amide compound selected from Compound No. 1 to Compound No. 12, 1 part of difenoconazole, 35 parts of a mixture (weight ratio 1:1) of white carbon and ammonium polyoxyethylene alkyl ether sulfate are mixed with an appropriate amount of water so as to give a total amount of 100 parts, and then the mixture is finely-ground by a wet grinding method to obtain a flowable formulation.

Formulation Example 3

Ten (10) parts of the present amide compound selected from Compound No. 1 to Compound No. 12, 1 part of triadimenol, 35 parts of a mixture (weight ratio 1:1) of white carbon and ammonium polyoxyethylene alkyl ether sulfate are mixed with an appropriate amount of water so as to give a total amount of 100 parts, and then the mixture is finely-ground by a wet grinding method to obtain a flowable formulation.

Formulation Example 4

Ten (10) parts of the present amide compound selected from Compound No. 1 to Compound No. 12, 1 part of prothioconazol, 35 parts of a mixture (weight ratio 1:1) of white carbon and ammonium polyoxyethylene alkyl ether sulfate are mixed with an appropriate amount of water so as to give a total amount of 100 parts, and then the mixture is finely-ground by a wet grinding method to obtain a flowable formulation.

Formulation EXAMPLE 5

Ten (10) parts of the present amide compound selected from Compound No. 1 to Compound No. 12, 1 part of tritiConazole, 35 parts of a mixture (weight ratio 1:1) of white carbon and ammonium polyoxyethylene alkyl ether sulfate are mixed with an appropriate amount of water so as to give a total amount of 100 parts, and then the mixture is finely-ground by a wet grinding method to obtain a flowable formulation.

Formulation Example 6

Ten (10) parts of the present amide compound selected from Compound No. 1 to Compound No. 12, 1 part of ipconazole, 35 parts of a mixture (weight ratio 1:1) of white carbon and ammonium polyoxyethylene alkyl ether sulfate are mixed with an appropriate amount of water so as to give a total amount of 100 parts, and then the mixture is finely-ground by a wet grinding method to obtain a flowable formulation.

Formulation Example 7

Ten (10) parts of the present amide compound selected from Compound No. 1 to Compound No. 12, 1 part of tebuconazole, 1.5 parts of sorbitan trioleate, and 28 parts of an aqueous solution containing 2 parts of polyvinyl alcohol are mixed, and then the mixture is finely-ground by a wet grinding method. To this mixture is added an appropriate amount of an aqueous solution containing 0.05 parts of xanthane gum and 0.1 parts of magnesium aluminium silicate so as to give a total amount of 90 parts, and then 10 parts of propylene glycol is added thereto. The mixture is stirred to obtain a flowable formulation.

Formulation Example 8

Ten (10) parts of the present amide compound selected from Compound No. 1 to Compound No. 12, 1 part of difenoconazol, 1.5 parts of sorbitan trioleate, and 28 parts of an aqueous solution containing 2 parts of polyvinyl alcohol are mixed, and then the mixture is finely-ground by a wet grinding method. To this mixture is added an appropriate amount of an aqueous solution containing 0.05 parts of xanthane gum and 0.1 parts of magnesium aluminium silicate so as to give a total amount of 90 parts, and then 10 parts of propylene glycol is added thereto. The mixture is stirred to obtain a flowable formulation.

Formulation Example 9

Ten (10) parts of the present amide compound selected from Compound No. 1 to Compound No. 12, 1 part of triadimenol, 1.5 parts of sorbitan trioleate, and 28 parts of an aqueous solution containing 2 parts of polyvinyl alcohol are mixed, and then the mixture is finely-ground by a wet grinding method. To this mixture is added an appropriate amount of an aqueous solution containing 0.05 parts of xanthane gum and 0.1 parts of magnesium aluminium silicate so as to give a total amount of 90 parts, and then 10 parts of propylene glycol is added thereto. The mixture is stirred to obtain a flowable formulation.

Formulation Example 10

Ten (10) parts of the present amide compound selected from Compound No. 1 to Compound No. 12, 1 part of prothioconazole, 1.5 parts of sorbitan trioleate, and 28 parts of an aqueous solution containing 2 parts of polyvinyl alcohol are mixed, and then the mixture is finely-ground by a wet grinding method. To this mixture is added an appropriate amount of an aqueous solution containing 0.05 parts of xanthane gum and 0.1 parts of magnesium aluminium silicate so as to give a total amount of 90 parts, and then 10 parts of propylene glycol is added thereto. The mixture is stirred to obtain a flowable formulation.

Formulation Example 11

Ten (10) parts of the present amide compound selected from Compound No. 1 to Compound No. 12, 1 part of triticonazole, 1.5 parts of sorbitan trioleate, and 28 parts of an aqueous solution containing 2 parts of polyvinyl alcohol are mixed, and then the mixture is finely-ground by a wet grinding method. To this mixture is added an appropriate amount of an aqueous solution containing 0.05 parts of xanthane gum and 0.1 parts of magnesium aluminium silicate so as to give a total amount of 90 parts, and then 10 parts of propylene glycol is added thereto. The mixture is stirred to obtain a flowable formulation.

Formulation Example 12

Ten (10) parts of the present amide compound selected from Compound No. 1 to Compound No. 12, 1 part of ipconazole, 1.5 parts of sorbitan trioleate, and 28 parts of an aqueous solution containing 2 parts of polyvinyl alcohol are mixed, and then the mixture is finely-ground by a wet grinding method. To this mixture is added an appropriate amount of an aqueous solution containing 0.05 parts of xanthane gum and 0.1 parts of magnesium aluminium silicate so as to give a total amount of 90 parts, and then 10 parts of propylene glycol is added thereto. The mixture is stirred to obtain a flowable formulation.

Formulation Example 13

Ten (10) parts of the present amide compound selected from Compound No. 1 to Compound No. 12, 2 parts of tebuconazole, 3 parts of calcium lignin sulfonate, 2 parts of sodium lauryl sulfate, and the rest parts of synthetic hydrated silicon oxide are well mixed while grinding to obtain 100 parts of a wettable powder.

Formulation Example 14

Ten (10) parts of the present amide compound selected from Compound No. 1 to Compound No. 12, 2 parts of difenoconazole, 3 parts of calcium lignin sulfonate, 2 parts of sodium lauryl sulfate, and the rest parts of synthetic hydrated silicon oxide are well mixed while grinding to obtain 100 parts of a wettable powder.

Formulation Example 15

Ten (10) parts of the present amide compound selected from Compound No. 1 to Compound No. 12, 2 parts of triadimenol, 3 parts of calcium lignin sulfonate, 2 parts of sodium lauryl sulfate, and the rest parts of synthetic hydrated silicon oxide are well mixed while grinding to obtain 100 parts of a wettable powder.

Formulation Example 16

Ten (10) parts of the present amide compound selected from Compound No. 1 to Compound No. 12, 2 parts of prothioconazole, 3 parts of calcium lignin sulfonate, 2 parts of sodium lauryl sulfate, and the rest parts of synthetic hydrated silicon oxide are well mixed while grinding to obtain 100 parts of a wettable powder.

Formulation Example 17

Ten (10) parts of the present amide compound selected from Compound No. 1 to Compound No. 12, 2 parts of triticonazole, 3 parts of calcium lignin sulfonate, 2 parts of sodium lauryl sulfate, and the rest parts of synthetic hydrated silicon oxide are well mixed while grinding to obtain 100 parts of a wettable powder.

Formulation Example 18

Ten (10) parts of the present amide compound selected from Compound No. 1 to Compound No. 12, 2 parts of ipconazole, 3 parts of calcium lignin sulfonate, 2 parts of sodium lauryl sulfate, and the rest parts of synthetic hydrated silicon oxide are well mixed while grinding to obtain 100 parts of a wettable powder.

Formulation Example 19

Ten (10) parts of the present amide compound selected from Compound No. 1 to Compound No. 12, 1 part of metconazole, 35 parts of a mixture (weight ratio 1:1) of white carbon and ammonium polyoxyethylene alkyl ether sulfate are mixed with an appropriate amount of water so as to give a total amount of 100 parts, and then the mixture is finely-ground by a wet grinding method to obtain a flowable formulation.

Formulation Example 20

Ten (10) parts of the present amide compound selected from Compound No. 1 to Compound No. 12, 1 part of metconazole, 1.5 parts of sorbitan trioleate, and 28 parts of an aqueous solution containing 2 parts of polyvinyl alcohol are mixed, and then the mixture is finely-ground by a wet grinding method. To this mixture is added an appropriate amount of an aqueous solution containing 0.05 parts of xanthane gum and 0.1 parts of magnesium aluminium silicate so as to give a total amount of 90 parts, and then 10 parts of propylene glycol is added thereto. The mixture is stirred to obtain a flowable formulation.

Formulation Example 21

Ten (10) parts of the present amide compound selected from Compound No. 1 to Compound No. 12, 2 parts of metconazole, 3 parts of calcium lignin sulfonate, 2 parts of sodium lauryl sulfate, and the rest parts of synthetic hydrated silicon oxide are well mixed while grinding to obtain 100 parts of a wettable powder.

Treatment Example 1

The flowable formulation prepared in Formulation example 1 is used for a smear treatment in an amount of 500 ml per 100 kg of dried sorghum seeds by using a rotary seed treatment machine (seed dresser, produced by Hans-Ulrich Hege GmbH) to obtain the treated seeds.

The seeds treated with each of the flowable formulations prepared in Formulation examples 2 to 12 are obtained in a manner similar to the above, by using the flowable formulations prepared in Formulation examples 2 to 12 instead of the flowable formulation prepared in Formulation example 1.

Treatment Example 2

The flowable formulation prepared in Formulation example 1 is used for a smear treatment in an amount of 40 ml per 10 kg of dried corn seeds by using a rotary seed treatment machine (seed dresser, produced by Hans-Ulrich Hege GmbH) to obtain the treated seeds.

The seeds treated with each of the flowable formulations prepared in Formulation examples 2 to 12 are obtained in a manner similar to the above, by using the flowable formulations prepared in Formulation examples 2 to 12 instead of the flowable formulation prepared in Formulation example 1.

Treatment Example 3

The wettable powder prepared in Formulation example 13 is used for powder coating treatment in an amount of 50 g per 10 kg of dried corn seeds to obtain the treated seeds.

The seeds treated with each of the wettable powders prepared in Formulation examples 14 to 18 are obtained in a manner similar to the above, by using the wettable powders prepared in Formulation examples 14 to 18 instead of the wettable powder prepared in Formulation example 13.

Treatment Example 4

The flowable formulation prepared in Formulation example 1 is used for a smear treatment in an amount of 50 ml per 10 kg of dried soybean seeds by using a rotary seed treatment machine (seed dresser, produced by Hans-Ulrich Hege GmbH) to obtain the treated seeds.

The seeds treated with each of the flowable formulations prepared in Formulation examples 2 to 12 are obtained in a manner similar to the above, by using the flowable formulations prepared in Formulation examples 2 to 12 instead of the flowable formulation prepared in Formulation example 1.

Next, the effect of the present invention is shown in Test examples.

Test Example 1

The present amide compound (No. 3) 10 mg and tebuconazole or triticonazole 1 mg were mixed, and thereto were added 150 microliters of slurry that was prepared by mixing 10 parts of Color Coat Red (manufactured by Becker Underwood Inc.: coloring agent), 10 parts of CF-CLEAR (manufactured by Becker Underwood Inc.: spreading agent) and an appropriate amount of water so as to give a total amount of 100 parts and the resulting mixture was then mixed thoroughly and 7.5 µL of the mixture was added to 1 g of wheat seeds and the resulting mixture was then agitated. After air drying, the treated wheat seeds were seeded into a 85 mL plastic cup in a ratio of about 10 grains per the cup.

At 12 days post the seeding, spores of *Puccinia recondita* were inoculated into the cups, and then the cups were placed under a dark and humid condition at 23° C. for 24 hours (hereinafter, referred to as a "treated group"). At 7 days post the inoculation, a ratio of the symptom area of the second leaves to the total area of the second leaves was observed.

On the other hand, the same seeding and inoculation was carried out using, wheat seeds without the above-mentioned treatment (hereinafter, referred to as an "untreated group"), and at 7 days post the inoculation, a ratio of the symptom area of the second leaves to the total area of the second leaves was observed.

From the results of the observation of the treated group and the untreated group, a control effect in the treated group was calculated by the following equation 1). The two duplicate tests were performed. The average value is shown in Table 2.

Control value (%)=(1−(Ratio of Symptom area of the second leaves to Total area of the second leaves in Treated group)/(Ratio of Symptom area of the second leaves to Total area of the second leaves in Untreated group))×100    Equation 1):

TABLE 2

| Test compounds | Dose (g/100 kg of seeds) | Control value (%) |
|---|---|---|
| Present compound (Compound No. 3) + Tebuconazole | 50 + 5 | 96 |
| Present compound (Compound No. 3) + Triticonazole | 50 + 5 | 97 |

Test Example 2

The present amide compound (No. 3) 10 mg and tebuconazole or triticonazole 1 mg were mixed and thereto were added 150 microliters of slurry that was prepared by mixing 10 parts of Color Coat Red (manufactured by Becker Underwood Inc.: coloring agent), 10 parts of CF-CLEAR (manufactured by Becker Underwood Inc.: spreading agent) and an appropriate amount of water so as to give a total amount of 100 parts and the resulting mixture was then mixed thoroughly, and 37.5 μL of the mixture was added to 5 g of corn seeds and the resulting mixture was then agitated. After air drying, the treated corn seeds were seeded into a 300 mL plastic cup in a ratio of 5 grains per the cup, and then covered with soil which had been mixed with a wheat bran culture of *Fusarium graminearum* (hereinafter, referred to as a "treated group"). At 18 days post the seeding, the number of seeds which failed to germinate was observed.

On the other hand, the same seeding was carried out using corn seeds without the above-mentioned treatment (hereinafter, referred to as an "untreated group"), and at 18 days post the seeding, the number of seeds which failed to germinate was observed.

From the results of the observation of the treated group and the untreated group, a control value was calculated by the following equation 2).

Control value (%)=(1−(Ratio of seeds failed to germinate to Total number of sown seeds in Treated group)/(Ratio of seeds failed to germinate to Total number of sown seeds in Untreated group))×100    Equation 2)

TABLE 3

| Test compounds | Dose (g/100 kg of seeds) | Control value (%) |
| --- | --- | --- |
| Present compound (Compound No. 3) + Tebuconazole | 50 + 5 | 100 |
| Present compound (Compound No. 3) + Triticonazole | 50 + 5 | 100 |

Test Example 3

The present amide compound (No. 3) or the present amide compound (No. 12) 10 mg and triticonazole, prothioconazole or metconazole 1 mg were mixed, and thereto were added 150 microliters of slurry that was prepared by mixing 10 parts of Color Coat Red (manufactured by Becker Underwood Inc.: coloring agent), 10 parts of CF-CLEAR (manufactured by Becker Underwood Inc.: spreading agent) and an appropriate amount of water so as to give a total amount of 100 parts and the resulting mixture was then mixed thoroughly and 7.5 μL of the mixture was added to 1 g of wheat seeds and the resulting mixture was then agitated. After air drying, the treated wheat seeds were seeded into a 85 mL plastic cup in a ratio of about 10 grains per the cup.

At 12 days post the seeding, spores of *Puccinia recondita* were inoculated into the cups, and then the cups were placed under a dark and humid condition at 23° C. for 24 hours (hereinafter, referred to as a "treated group"). At 7 days post the inoculation, a ratio of the symptom area of the second leaves to the total area of the second leaves was observed.

On the other hand, the same seeding and inoculation was carried out using wheat seeds without the above-mentioned treatment (hereinafter, referred to as an "untreated group"), and at 7 days post the inoculation, a ratio of the symptom area of the second leaves to the total area of the second leaves was observed.

From the results of the observation of the treated group and the untreated group, a control effect in the treated group was calculated by the above equation 1). The two duplicate tests were performed. The average value is shown in Table 4.

TABLE 4

| Test compounds | Dose (g/100 kg of seeds) | Control value (%) |
| --- | --- | --- |
| Present compound (Compound No. 12) + Triticonazole | 50 + 5 | 100 |
| Present compound (Compound No. 12) + Prothioconazole | 50 + 5 | 83 |
| Present compound (Compound No. 3) + Metconazole | 50 + 5 | 83 |
| Present compound (Compound No. 12) + Metconazole | 50 + 5 | 92 |

Test Example 4

The present amide compound (No. 12) 10 mg and triticonazole 1 mg were mixed and thereto were added 150 microliters of slurry that was prepared by mixing 10 parts of Color Coat Red (manufactured by Becker Underwood Inc.: coloring agent), 10 parts of CF-CLEAR (manufactured by Becker Underwood Inc.: spreading agent) and an appropriate amount of water so as to give a total amount of 100 parts and the resulting mixture was then mixed thoroughly, and 37.5 μL of the mixture was added to 5 g of corn seeds and the resulting mixture was then agitated. After air drying, the treated corn seeds were seeded into a 300 mL plastic cup in a ratio of 5 grains per the cup, and then covered with soil which had been mixed with a wheat bran culture of *Fusarium graminearum* (hereinafter, referred to as "treated group"). At 18 days post the seeding, the number of seeds which failed to germinate was observed.

On the other hand, the same seeding was carried out using corn seeds without the above-mentioned treatment (hereinafter, referred to as an "untreated group"), and at 18 days post the seeding, the number of seeds which failed to germinate was observed.

From the results of the observation of the treated group and the untreated group, a control value was calculated by the above equation 2).

TABLE 5

| Test compounds | Dose (g/100 kg of seeds) | Control value (%) |
| --- | --- | --- |
| Present compound (Compound No. 12) + Triticonazole | 50 + 5 | 86 |

The invention claimed is:

1. A composition for controlling plant diseases comprising an amide compound represented by a formula (I):

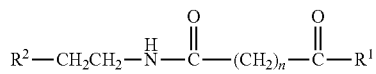

(I)

wherein
n is 3 or 4;
R¹ represents a hydroxy group or a C1-C6 alkoxy group;
R² represents an optionally substituted phenyl group or an optionally substituted 3-indolyl group, and the phenyl group or the 3-indolyl group being represented by the R² may be substituted on the carbon atoms independently of each other with one or more substituents selected from the group consisting of a halogen atom, a hydroxy group, a nitro group, a C1-C6 alkyl group or a C1-C6 alkoxy group;
or salts thereof and
at least one kind of azole compounds selected from the group consisting of tebuconazole, difenoconazole, triticonazole, imazalil, triadimenol, fluquinconazole, prochloraz, prothioconazole, diniconazole, diniconazole M, cyproconazole, tetraconazole, ipconazole, oxpoconazole fumarate, pefurazoate, triflumizole, azaconazole, bitertanol, bromuconazole, epoxiconazole, fenbuconazole, flusilazole, flutriafol, hexaconazole, imibenconazole, myclobutanil, penconazole, propiconazole, simeconazole, triadimefon and metconazole, and
wherein a weight ratio of the amide compound or salts thereof to the azole compounds is in the range of 100:1 to 10:1.

2. The composition for controlling plant diseases according to claim 1 wherein at least one kind of azole compounds is selected from the group consisting of tebuconazole, difenoconazole, triticonazole, imazalil, triadimenol, fluquinconazole, prochloraz, prothioconazole, diniconazole, diniconazole M, cyproconazole, tetraconazole, ipconazole, oxpoconazole fumarate, pefurazoate, triflumizole, azaconazole, bitertanol, bromuconazole, epoxiconazole, fenbuconazole, flusilazole, flutriafol, hexaconazole, imibenconazole, myclobutanil, penconazole, propiconazole, simeconazole and triadimefon.

3. A method for controlling plant diseases which comprises applying an effective amount of the composition for controlling plant diseases according to claim 1 to a plant or a soil for cultivating the plant.

4. A method for controlling plant diseases which comprises applying an effective amount of the composition for controlling plant diseases according to claim 1 to plant seeds.

5. The method for controlling plant diseases according to claim 4 wherein the plant seeds are seeds of corn, cotton, soybean, beet, rapeseed, wheat or rice.

6. A method for controlling plant diseases which comprises applying an effective amount of the composition for controlling plant diseases according to claim 2 to a plant or a soil for cultivating the plant.

7. A method for controlling plant diseases which comprises applying an effective amount of the composition for controlling plant diseases according to claim 2 to plant seeds.

8. The method for controlling plant diseases according to claim 7 wherein the plant seeds are seeds of corn, cotton, soybean, beet, rapeseed, wheat or rice.

* * * * *